United States Patent
Kawai

(10) Patent No.: US 9,437,999 B2
(45) Date of Patent: *Sep. 6, 2016

(54) METHOD FOR MANUFACTURING OXYGEN SENSOR

(75) Inventor: Masashi Kawai, Miyoshi (JP)

(73) Assignee: TOYOTA JIDOSHA KABUSHIKI KAISHA, Toyota-shi, Aichi (JP)

( * ) Notice: Subject to any disclaimer, the term of this patent is extended or adjusted under 35 U.S.C. 154(b) by 280 days.

This patent is subject to a terminal disclaimer.

(21) Appl. No.: 14/232,335

(22) PCT Filed: Jul. 12, 2012

(86) PCT No.: PCT/JP2012/004507
§ 371 (c)(1),
(2), (4) Date: Jan. 13, 2014

(87) PCT Pub. No.: WO2013/021549
PCT Pub. Date: Feb. 14, 2013

(65) Prior Publication Data
US 2014/0137404 A1   May 22, 2014

(30) Foreign Application Priority Data

Aug. 10, 2011   (JP) .................. 2011-175060

(51) Int. Cl.
*H01R 43/16*   (2006.01)
*G01N 27/407*   (2006.01)

(52) U.S. Cl.
CPC .......... *H01R 43/16* (2013.01); *G01N 27/4075* (2013.01); *Y10T 29/49224* (2015.01)

(58) Field of Classification Search
CPC .......... B05D 5/04; B05D 5/12; C23C 14/58; C23C 16/56; G01N 27/407; G01N 27/4075; H01R 43/16; Y10T 29/49224
See application file for complete search history.

(56) References Cited

U.S. PATENT DOCUMENTS

| 4,253,931 A | 3/1981 | Gold et al. |
| 4,477,487 A | 10/1984 | Kojima et al. |

(Continued)

FOREIGN PATENT DOCUMENTS

| GB | 1 505 983 A | 4/1978 |
| GB | 2162324 A | 1/1986 |

(Continued)

OTHER PUBLICATIONS

Communication dated Jan. 27, 2015, issued by the U.S. Patent and Trademark Office in corresponding U.S. Appl. No. 14/127,033.

(Continued)

*Primary Examiner* — Carl Arbes
(74) *Attorney, Agent, or Firm* — Sughrue Mion, PLLC

(57) ABSTRACT

The invention provides a method for manufacturing an oxygen sensor that is excellent in responsiveness and can be preferably used for diagnosis of catalyst deterioration. An oxygen sensor 1 equipped with an oxygen sensor element 11 comprising a solid electrolyte 21 and Pt coatings, as a pair of electrodes, on both surfaces of the solid electrolyte 21 is manufactured. The method comprises at least steps of: providing a Pt coating 23 on at least one of the solid electrolyte 21 surfaces exposed to the gas to be tested so as to form closed pores 23*a* inside the Pt coating 23; and heating either the Pt coating 23 or 24 exposed to gas to be tested in a gas atmosphere with higher oxygen concentration than that of the atmospheric gas.

2 Claims, 4 Drawing Sheets

(56) References Cited

U.S. PATENT DOCUMENTS

| | | | |
|---|---|---|---|
| 4,655,892 A | 4/1987 | Satta et al. | |
| 4,940,528 A | 7/1990 | Oki et al. | |
| 6,025,205 A | 2/2000 | Park et al. | |
| 6,071,554 A | 6/2000 | Isomura et al. | |
| 6,306,457 B1 | 10/2001 | Schneider et al. | |
| 6,344,118 B1 * | 2/2002 | Kobayashi | G01N 27/4075 204/421 |
| 9,134,268 B2 * | 9/2015 | Kawai | G01N 27/4075 |
| 2002/0121441 A1 | 9/2002 | Reidmeyer et al. | |

FOREIGN PATENT DOCUMENTS

| | | |
|---|---|---|
| JP | 57207856 A | 12/1982 |
| JP | 61120055 A | 6/1986 |
| JP | 01-185440 A | 7/1989 |
| JP | 05099895 A | 4/1993 |
| JP | 08-20404 B2 | 3/1996 |
| JP | 09-264871 A | 10/1997 |
| JP | H11326267 A * | 11/1999 |
| JP | 2000-105213 A | 4/2000 |
| JP | 3094382 A | 10/2000 |
| JP | 3094382 B2 | 10/2000 |
| JP | 2000277818 A | 10/2000 |
| JP | 2002-228622 A | 8/2002 |
| JP | 2013003051 A | 1/2013 |
| WO | 2012176063 A1 | 12/2012 |

OTHER PUBLICATIONS

Communication dated Sep. 30, 2014, issued by the U.S. Patent and Trademark Office in corresponding U.S. Appl. No. 14/127,033.
Communication dated May 13, 2015, issued by the U.S. Patent and Trademark Office in corresponding U.S. Appl. No. 14/127,033.

* cited by examiner (a)

(b)

(a)

(b)

METHOD FOR MANUFACTURING OXYGEN SENSOR

CROSS REFERENCE TO RELATED APPLICATIONS

This application is a National Stage of International Application No. PCT/JP2012/004507, filed Jul. 12, 2012, claiming priority from Japanese Patent Application No. 2011-175060, filed Aug. 10, 2011, the contents of all of which are incorporated herein by reference in their entirety.

TECHNICAL FIELD

The present invention relates to a method for manufacturing an oxygen sensor equipped with a Pt-coated oxygen sensor element. More particularly, the present invention relates to a method for manufacturing an oxygen sensor that is excellent in detection accuracy.

BACKGROUND ART

Oxygen sensors ($O_2$ sensors) have heretofore been equipped with oxygen sensor elements, and the oxygen sensor elements have been accommodated in housing. In the case of bottomed cylindrical (cup-like) oxygen sensor elements, for example, an oxygen sensor element equipped with an oxygen-ion-conductive cup-like solid electrolyte, an internal electrode provided on the inner surface of the solid electrolyte, and an external electrode provided on the outer surface of the solid electrolyte are generally known.

While such oxygen sensor element brings an internal electrode into contact with the air such that the internal electrode serves as a reference electrode, it brings an external electrode into contact with a gas to be tested such that the external electrode serves as a measurement electrode. Thus, oxygen concentration in the exhaust gas from the internal combustion engine is measured.

In recent years, a variety of studies have been conducted on external electrodes in order to improve the performance of the oxygen sensor element. For example, an oxygen sensor element exhibiting improvement in the average particle diameter for crystalline materials of an external electrode and in the film thickness of the external electrode aimed at improvement in low-temperature operability and gas responsiveness has been disclosed (see, for example, Patent Document 1 or 2). According to such disclosure, a solid electrolyte constituting an oxygen sensor element is composed of stabilized zirconia, and a platinum (Pt) coating is provided on the solid electrolyte surface as an electrode material.

For example, an oxygen sensor comprising a solid electrolyte plated with a nonporous Pt cermet coating as a platinum coating used for an electrode has been proposed (see, for example, Patent Document 3). Another technique (i.e., an oxygen sensor comprising a solid electrolyte coated, on its surface, with a paste containing platinum particles via thermal treatment) has been proposed (see, for example, Patent Document 4). A further technique (i.e., an oxygen sensor prepared by allowing a platinum nucleus to deposit on a solid electrolyte surface, bringing a plating solution containing a platinum complex salt into contact with the nucleus to provide a plated coating, and heating the resultant to prepare a porous coating having open pores) has been proposed (see, for example, Patent Document 5).

CITATION LIST

Patent Literature

PTL 1: JP Patent Publication (Kokoku) No. H08-20404 B (1996)
PTL 2: JP Patent Publication (Kokai) No. H01-185440 A (1989)
PTL 3: JP Patent Publication (Kokai) No. 2000-105213 A
PTL 4: JP Patent Publication (Kokai) No. 2002-228622 A
PTL 5: JP Patent Publication (Kokai) No. H09-264871 A (1997)

SUMMARY OF INVENTION

Technical Problem

It is preferable that the output voltage of an oxygen sensor element change immediately after the lean gas atmosphere is converted into a rich gas atmosphere or vice versa, regardless of the gas concentration. However, the tracking capacity (responsiveness) of existing oxygen sensor elements described above cannot be regarded as sufficient. Accordingly, stable provision of an oxygen sensor equipped with an oxygen sensor element having excellent responsiveness (to a lean gas, in particular), high sensitivity, and high accuracy is desired from the viewpoint of exhaust gas regulation, fuel efficiency, low cost, and the like for the future.

In general, an oxygen sensor shows changes in gas atmospheres subjected to measurement as an output value based on the amount of oxygen in the air. Thus, the capacity for rapidly changing the oxygen conditions at the solid electrolyte interface via an electrode provided on the surface comprising gas to be tested determines the tracking capacity of the output voltage of the oxygen sensor. Since the oxygen conditions rapidly change in a rich gas atmosphere, the responsiveness described above would not be an issue of concern.

In a lean gas atmosphere subjected to measurement, however, the reaction time of the oxygen sensor element tends to be prolonged as the oxygen conditions change. This may occasionally cause a temporary difference between the oxygen concentration of the gas to be tested and the output voltage of the oxygen sensor. This occasionally lowers the controllability of air-fuel ratio, and it may consequently reduce internal combustion engine emissions.

The air-fuel ratio control of the automobile internal combustion engine controls through feedback the amount of fuels ejected based on the output signal of the A/F sensor located upstream of a catalyst, so that the air-fuel ratio of the exhaust gas to be injected into the catalyst reaches the target air-fuel ratio (e.g., the theoretical air-fuel ratio), in order to cope with the tighter control on exhaust emissions.

In contrast, an oxygen sensor is located downstream of the catalyst. Since the oxygen sensor is characterized by rapid changes in output voltage at a level close to the theoretical air-fuel ratio (the stoichiometric value), the target output value of the A/F sensor is corrected based on the output voltage of an oxygen sensor element, and output signal errors caused by the deteriorated A/F sensor are corrected.

By performing such control through feedback, the amount of fuels ejected from an injector is adjusted so as to bring the air-fuel ratio of the air injected to a level of the target air-fuel ratio (e.g., the theoretical air-fuel ratio), and exhaust gas emissions are thus reduced.

When diagnosis of catalyst deterioration is controlled (i.e., on-board diagnosis (OBD) control) based on the control through feedback described above, in general, techniques such as a Cmax method or trajectory length method are employed. Such techniques involve the use of the hysteresis loop created by the air-fuel ratio and the output of the oxygen sensor to estimate the oxygen storage capacity in catalysts, and catalyst deterioration is diagnosed based on the results. Accordingly, a certain extra response time is required for exhibition of oxygen sensor properties.

As described above, however, it is most preferable that both the lean/rich response speeds be high from the viewpoint of emission. In such a case, the curve obtained by the air-fuel ratio and the output of the oxygen sensor forms a Z-like shape without a hysteresis loop. Thus, it is difficult to apply the same conditions to OBD control.

The present invention has been made based on such points of view. The present invention is intended to provide a method for manufacturing an oxygen sensor that is excellent in responsiveness and that can be suitably used for diagnosis of catalyst deterioration.

Solution to Problem

Under the above circumstances, the present inventors have conducted concentrated studies. As a result, they consider that a preferable oxygen sensor would have sensor properties that would make responsiveness to a lean gas (i.e., the responsiveness at the time of conversion from a rich gas into a lean gas) more rapid and make responsiveness to a rich gas (i.e., the responsiveness at the time of conversion from a lean gas into a rich gas) equivalent to or slower than that of conventional sensors (i.e., response time is made somewhat slower than that of conventional sensors).

They discovered that diagnosis of catalyst deterioration can be accurately controlled by enhancing responsiveness to a lean gas with the use of an oxygen sensor having sensor properties as described above to reduce internal combustion engine emissions and fuel consumption and making the responsiveness to a rich gas moderate.

The present invention has been completed based on the novel finding described above. It relates to a method for manufacturing an oxygen sensor equipped with Pt-coated oxygen sensor elements on both solid electrolyte surfaces as a pair of electrodes. The method is characterized by at least comprising a step of applying a Pt coating on at least one of the solid electrolyte surfaces exposed to a gas to be tested, so as to form closed pores inside the Pt coating, and a step of heating the Pt coating provided on a surface exposed to the gas to be tested in a gas atmosphere with higher oxygen concentration than that of the atmospheric gas.

In the step of coating, Pt coatings are provided as a pair of electrodes on both surfaces of the sensor element of the oxygen sensor provided by the present invention. Closed pores are formed inside of at least the Pt coating provided on the surface exposed to the gas to be tested (i.e., the exhaust gas). Subsequently, the Pt coating provided on the surface exposed to the gas to be tested is heated in a gas atmosphere with higher oxygen concentration than that of the atmospheric gas in the step of heating. It is thus considered that oxygen gas penetrates and diffuses towards the inside of the closed pores from the Pt coating surface, the insides of the closed pores are filled with gas with higher oxygen concentration than that of the atmospheric gas, and oxygen atoms adsorb to the platinum atoms in the vicinity of the closed pores.

In a rich gas atmosphere (an exhaust gas containing HC, $H_2$, and CO), in general, the oxygen concentration at the three-phase interface at which the solid electrolyte, the Pt coating, and oxygen in the exhaust gas react with one another is lower than that in the lean gas (an exhaust gas containing NOx) atmosphere. When the atmosphere of the exhaust gas as the gas to be tested is converted from the rich gas atmosphere into a lean gas atmosphere, the oxygen concentration at the three-phase interface is elevated.

According to this embodiment, oxygen is present inside the closed pores of a Pt coating and in the vicinity thereof when a rich gas atmosphere is converted into a lean gas atmosphere. Thus, oxygen supplied through the closed pores enables rapid elevation of the oxygen concentration at the three-phase interface. This can enhance responsiveness (sensitivity) to a lean gas. As a result, NOx contained in a lean gas can be rapidly detected. Thus, conversion from a rich gas atmosphere into a lean gas atmosphere can be controlled through feedback at an early stage, and performance of the internal combustion engine can be improved.

In a lean gas atmosphere, in general, the oxygen concentration at the three-phase interface is higher than that in a rich gas atmosphere. The oxygen concentration at the three-phase interface is lowered when a lean gas atmosphere is converted into a rich gas atmosphere.

According to this embodiment, oxygen atoms or molecules are present inside the closed pores of a Pt coating and in the vicinity thereof when a lean gas atmosphere is converted into a rich gas atmosphere. Thus, the oxygen concentration inside the closed pores of a Pt coating and in the vicinity thereof is lowered before the oxygen concentration at the three-phase interface is lowered. In addition, HC is oxidized on an electrode surface. Thus, oxygen inside closed pores of a Pt coating exhibits buffering effects on reactions at the three-phase interface (i.e., an oxygen-containing closed pore serves as a buffer phase).

This consequently creates a time lag, and moderate responsiveness to a rich gas can be achieved. Even if the responsiveness as described above is enhanced, accordingly, a hysteresis loop is formed by the air-fuel ratio and the oxygen sensor output, and diagnosis of catalyst deterioration (i.e., OBD control) can be accurately controlled based on the hysteresis loop. Thus, deterioration of noble metal catalysts can be adequately diagnosed, and cost advantages of noble metal catalysts can be improved.

Examples of gas atmospheres with higher oxygen concentration than that of the atmospheric gas include a gas atmosphere in which a partial oxygen gas pressure is higher than that of the atmospheric gas and a gas atmosphere in which an ozone gas with higher oxidizing properties is present in addition to the atmospheric gas. As long as oxygen can penetrate and spread from the Pt coating surface toward the closed pores in the process of heating described above, the gas atmosphere is not limited.

Examples of methods for coating a solid electrolyte surface with Pt include a method of providing a Pt paste coating, a method of forming a Pt coating via PVD or CVD, and a method of providing a Pt coating via plating, such as electrolytic plating, non-electrolytic plating, or hot-dip plating. Methods of coating are not particularly limited, as long as a Pt coating with closed pores is provided on the solid electrolyte surface.

According to a more preferable embodiment, the step of coating may be carried out via non-electrolytic platinum plating while bubbling the plating solution with a non-oxidizing gas to form the closed pores inside the Pt coating.

According to this embodiment, for example, a Pt coating can be easily provided even if a solid electrolyte has a complicated shape, such as a bottomed cylindrical shape. By bubbling the solution with a non-oxidizing gas, in addition, non-oxidizing gas bubbles adhere to a Pt coating surface during the process of film formation, and a Pt coating is formed in that state. Thus, closed pores can be easily provided inside the Pt coating.

Examples of gases that do not oxidize platinum (non-oxidizing gases) include gases such as hydrogen gas and nitrogen gas and inert gases such as helium gas and argon gas. When an oxidizing gas containing oxygen or ozone is used as a gas that oxidizes platinum, a Pt coating cannot be formed via non-electrolytic plating.

If oxygen gas penetrates closed pores and the closed pores are then filled (or sealed) with a gas with higher oxygen concentration than that of the atmospheric gas as described above, heating conditions are not particularly limited. According to a preferable embodiment, the step of heating is carried out at 1,000 degrees C. to 1,300 degrees C. for at least 1 hour.

According to this embodiment, heating may be carried out in a gas atmosphere with higher oxygen concentration than that of the atmospheric gas under the heating conditions described above (i.e., a platinum coating is subjected to the aging treatment) to arrange the crystal orientation of the Pt coating on the (001) surface.

More specifically, the aging treatment described above leads to changes in the crystal orientation of the electrode (the Pt coating) exposed to the gas to be tested, and the electrode has a structure with an increased (001) surface area that is advantageous for oxygen dissociation and adsorption. This further improves oxygen dissociation and adsorption at the electrode, and an oxygen sensor comprising a built-in oxygen sensor element is thus capable of improving responsiveness (sensitivity) to a lean gas at a very low concentration in the exhaust gas.

While the crystal orientation of crystal grains constituting the Pt coating provided via non-electrolytic platinum plating is deduced to develop at random or toward the direction {111}, in particular, the crystal orientation of the Pt coating can be easily arranged on a (001) surface that is advantageous for oxygen dissociation and adsorption even if the Pt coating is provided in such a manner, provided that heating is carried out within the temperature range described above.

As a result, changes in exhaust gas atmospheres can be controlled through feedback at an early stage, the engine system can be stably controlled, and fuel consumption and internal combustion engine emissions can be reduced compared with conventional oxygen sensors.

In addition, the electrode and the electrode/solid electrolyte interface are tempered via heating, and the texture is then stabilized. As a result, the electrode is stabilized in an active state (i.e., a condition that is less likely to change depending on the temperature at which the sensor is used), and changes in sensor properties with the elapse of time are reduced compared with conventional techniques.

When heating is carried out at a temperature lower than 1,000 degrees C. or for less than 1 hour, the area of the (001) surface on which the Pt coating is provided may not be sufficiently large. When the heating temperature is higher than 1,300 degrees C., in contrast, electrode deterioration may be accelerated due to progress in Pt aggregation.

According to a more preferable embodiment, the step of heating is carried out in a gas atmosphere containing 50% or more oxygen by volume. According to this embodiment, the crystal orientation changes as a result of heating for approximately 1 hour, and an electrode with the increased (001) surface area can be obtained.

The present application also discloses an oxygen sensor having properties as described above. The oxygen sensor of the present invention is equipped with an oxygen sensor element comprising a solid electrolyte and Pt coatings, as a pair of electrodes, on both surfaces thereof. Closed pores are formed inside the Pt coating provided on at least one of the solid electrolyte surfaces exposed to the gas to be tested, and the closed pores are filled with gas with higher oxygen concentration than that of the atmospheric gas.

According to the present invention, closed pores are formed inside the Pt coating exposed to the gas to be tested of the oxygen sensor element, and the closed pores are filled with gas with higher oxygen concentration than that of the atmospheric gas. When a lean gas atmosphere is converted into a rich gas atmosphere, as described above, a closed pore on the Pt coating functions as a buffer phase for the reaction at the three-phase interface. As a result, moderate responsiveness to a rich gas is achieved, and diagnosis of catalyst deterioration can be accurately controlled (OBD control).

When a rich gas atmosphere is converted into a lean gas atmosphere, in contrast, responsiveness (sensitivity) to a lean gas is improved. Thus, changes of the rich gas atmosphere into a lean gas atmosphere can be controlled through feedback at an early stage, and the performance of the internal combustion engine can be further improved.

Advantageous Effects of Invention

According to the present invention, an oxygen sensor that is excellent in responsiveness and can be preferably used for diagnosis of catalyst deterioration can be obtained.

BRIEF DESCRIPTION OF DRAWINGS

FIG. 2(a) is a cross-sectional view of the oxygen sensor according to the example, and FIG. 2(b) is a cross-sectional view of that according to the comparative example.

FIG. 3(a) shows an inverse pole figure for electrodes (Pt coatings) provided on the oxygen sensor elements analyzed via EBSD according to Reference Example 2, and FIG. 3(b) shows the same according to a comparative example.

DESCRIPTION OF EMBODIMENTS

An embodiment of the method for manufacturing the oxygen sensor according to an embodiment of the present invention (the $O_2$ sensor) is described below.

Figure 1:
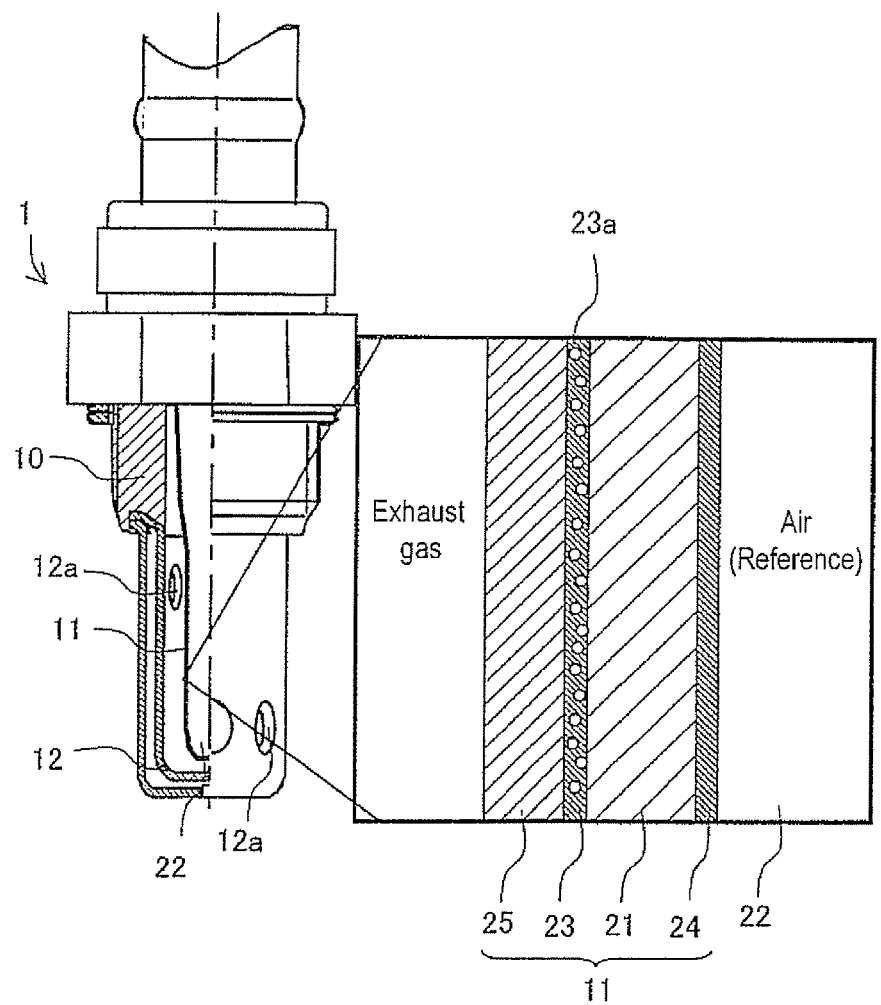
FIG. 1 is a schematic cross-sectional view of the oxygen sensor according to an embodiment of the present invention and an oxygen sensor element built in the oxygen sensor.

FIG. 1 is a schematic cross-sectional view of the oxygen sensor according to an embodiment of the present invention and an oxygen sensor element built in the oxygen sensor. As shown in FIG. 1, the oxygen sensor 1 according to an embodiment of the present invention is provided in an exhaust pipe of the internal combustion engine, it detects the concentration of oxygen or unburnt gas in the exhaust gas from the internal combustion engine, and it detects the air-fuel ratio in the combustion chamber of the internal combustion engine based on the concentration of oxygen or unburnt gas.

Specifically, the oxygen sensor 1 comprises the built-in oxygen sensor element 11, and the oxygen sensor element 11 is introduced and fixed in the housing 10. An end of the oxygen sensor element 11 is protected with the two-tiered cover 12 for the gas to be tested. The cover 12 for the gas to be tested is provided with the introduction port 12a for the gas to be tested that introduces the gas to be tested (i.e., the exhaust gas). This allows introduction of the gas to be tested into the external electrode 23 provided in the cover 12 for the gas to be tested described below.

The oxygen sensor element 11 is at least equipped with, for example, the bottomed cylindrical (a cup-like shape) solid electrolyte 21 and a pair of electrodes 23 and 24 on both surfaces of the solid electrolyte 21. Electrodes of the oxygen sensor element 11 are located within the cover 12 for the gas to be tested when mounted in the housing 10 of the oxygen sensor 1.

More specifically, a Pt coating serving as the external electrode 23 is provided on the outer surface of the gas sensor element 11, and a porous protective layer (or a diffusion-resistant layer) 25 covering the external electrode 23 is provided thereon.

Meanwhile, the oxygen sensor element 11 comprises an air chamber 22 that introduces the air thereinto, and the inner surface of the solid electrolyte 21 is covered by the internal electrode 24. Regarding the pair of electrodes 23 and 24 of the oxygen sensor element 11, the external electrode 23 is designed to be exposed to the gas to be tested and the internal electrode 24 is designed to be exposed to the reference gas (the air).

An example of a generally known oxygen sensor element is yttria-stabilized zirconia (YSZ). However, an oxygen sensor element is not particularly limited, provided that a material has ion conductivity and excellent heat resistance. In addition, the closed pores 23a are provided within the external electrode 23, and the insides of the closed pores 23a are filled (or sealed) with a gas having higher oxygen concentration than that of the atmospheric gas, as described above.

The oxygen sensor 1 is mounted on an exhaust pipe of the internal combustion engine. In this case, the internal electrode 24 exposed to the air serves as a reference electrode, and the external electrode 23 exposed to the exhaust gas serves as a measurement electrode. A concentration cell is formed due to differences in oxygen concentration between the external electrode 23 and the internal electrode 24. The oxygen concentration can be determined by measuring the potential difference (voltage) between electrodes.

When an exhaust gas is converted into a rich gas, for example, differences in oxygen concentration between the exhaust gas and the atmospheric gas become large, and the output voltage of the oxygen sensor increases. When an exhaust gas is converted into a lean gas, however, differences in oxygen concentration between the exhaust gas and the atmospheric gas become small, and the output voltage of the oxygen sensor decreases.

The method for manufacturing the oxygen sensor element 11 is hereafter described. At the outset, the bottomed cylindrical solid electrolyte 21 comprising yttria-stabilized zirconia (YSZ) in which the air chamber 22 is provided is molded.

Subsequently, a Pt coating is provided on the outer surface of the solid electrolyte 21 as the external electrode 23 so as to form the closed pores 23a inside the Pt coating via non-electrolytic platinum plating under a non-oxidizing gas atmosphere such as a hydrogen gas atmosphere (the step of coating).

Specifically, an aqueous platinum solution, such as an aqueous dinitrodiamineplatinum solution, is used as a plating solution, the solution is heated to a given temperature, an additive, such as a reducing agent, is introduced thereinto, and platinum is deposited on the outer surface of the solid electrolyte without shaking the solid electrolyte and/or a fixture holding the same. Thereafter, the resultant is rinsed and dried, and an external electrode 23 having a film thickness of 1 to 2 micrometers (the Pt coating) is then formed.

Closed pores 23a are formed while refraining from shaking a solid electrolyte and/or a fixture holding the solid electrolyte if the solid electrolyte and/or the fixture had been shaken in the past at the time of film formation. Alternatively, closed pores 23a are formed by introducing a reduced amount of stabilizer for plating or no stabilizer into a plating solution.

Alternatively, closed pores 23a are formed inside the external electrode 23 (the Pt coating) by providing a Pt coating at a speed faster than a conventional film-formation speed. For example, the concentration of an aqueous dinitrodiamineplatinum solution may be elevated, the pH level thereof may be adjusted, or the temperature of a plating solution may be increased, in comparison with conventional conditions.

According to the technique described above, hydrogen gas generated on a Pt coating is not discharged from the surface, and it remains in the form of air bubbles during the process of film formation. Accordingly, closed pores 23a (i.e., closed spaces that do not communicate with the outer air) are formed in a Pt coating provided in such a state, and the closed pores 23a can then be filled with a gas with higher oxygen concentration than that of the air by the subsequent step of heating. Pt coating thickness is likely to become somewhat greater due to the formation of crystal grains having closed pores and the influence imposed by the hydrogen gas generated.

In addition, closed pores 23a may be formed inside the Pt coating by bubbling a non-oxidizing gas such as hydrogen gas through a non-electrolytic platinum plating solution. By bubbling a non-oxidizing gas through the plating solution, non-oxidizing gas bubbles adhere to the Pt coating surface during film formation, and the Pt coating is formed in that state. Thus, closed pores 23a can be easily formed inside the Pt coating.

Since the molecular weight of hydrogen gas is low, hydrogen gas within the closed pores 23a can be easily discharged (i.e., replaced with an oxygen-containing gas described below) when hydrogen gas is used as a non-oxidizing gas.

The external electrode 23 is then heated under the atmospheric pressure at a given heating temperature (sintering temperature) (1,000 degrees C. to 1,200 degrees C.) for 1 hour to sinter platinum of the external electrode 23. Subsequently, a $MgAl_2O_4$ spinel porous protective layer is provided via plasma spray coating in order to protect the external electrode 23.

Further, the internal electrode 24 is provided on the inner surface of the solid electrolyte (element) via non-electrolytic platinum plating. The internal electrode 24 comprising a Pt coating may be provided on the inner surface of the solid electrolyte 21 when the external electrode 23 is provided. Alternatively, a coating may be provided by a general method, such as PVD or CVD, as in the past.

Subsequently, the oxygen sensor element 11 on which the external electrode 23 and the internal electrode 24 are formed is heated under a gas atmosphere with higher oxygen concentration than that of the atmospheric gas (preferably under an atmosphere in which the oxygen concentration is 50% by volume or higher or an atmosphere in which ozone gas is present) (the step of heating).

Since the Pt coating provided on the surface exposed to the gas to be tested is heated under a gas atmosphere with higher oxygen concentration than that of the atmospheric gas in the step of heating, the oxygen gas penetrates and spreads toward the inside of the closed pores 23$a$ from the Pt coating surface. Thereafter, the closed pores 23$a$ are filled with a gas with higher oxygen concentration than that of the atmospheric gas (i.e., gas that penetrates and spreads), and oxygen atoms are considered to adsorb to platinum atoms in the vicinity of the closed pores 23$a$.

Heating is carried out at a given heating temperature that is higher than the sintering temperature for the external electrode 23 (1,100 degrees C. to 1,300 degrees C.) for 1 hour or longer (i.e., the Pt coating is subjected to aging). Thus, the crystal orientation of the Pt coating of the external electrode 23 can be arranged in the direction of (001).

The oxygen sensor element 11 described above may be incorporated into the housing 10 as shown in FIG. 1, and the cover 12 for the gas to be tested is provided thereon. Thus, the oxygen sensor 1 can be obtained.

In a rich gas atmosphere (an exhaust gas containing HC, $H_2$, and CO), in general, the oxygen concentration at the three-phase interface where the solid electrolyte 21, the external electrode 23 (the Pt coating), and oxygen in the exhaust gas react with one another is lower than that in a lean gas atmosphere (an exhaust gas containing NOx). When a rich gas atmosphere is converted into a lean gas atmosphere, the oxygen concentration at the three-phase interface is elevated.

According to this embodiment, oxygen atoms or molecules exist inside the closed pores 23$a$ of the external electrode 23 (a Pt coating) and in the vicinity thereof when a lean gas atmosphere is converted into a rich gas atmosphere. Thus, the oxygen concentration inside the closed pores 23$a$ and in the vicinity thereof is lowered before the oxygen concentration at the three-phase interface is lowered. Specifically, an oxygen-containing closed pore 23$a$ serves as a buffer phase for a reaction at the three-phase interface. As a result, moderate responsiveness to a rich gas can be achieved, and diagnosis of catalyst deterioration (OBD) can be accurately controlled. This enables adequate diagnosis of deterioration of noble metal catalysts, and cost advantages of noble metal catalysts can be improved.

When a rich gas atmosphere is converted into a lean gas atmosphere, however, oxygen is present inside the closed pores 23$a$ of the external electrode 23 (a Pt coating) and in the vicinity thereof. Thus, the oxygen gas concentration at the three-phase interface can be elevated more rapidly. This can improve responsiveness (sensitivity) to a lean gas. Consequently, NOx contained in a lean gas can be detected more rapidly. This enables control through feedback of conversion from a rich gas atmosphere into a lean gas atmosphere at an early stage, and the performance of an internal combustion engine can be more improved.

When polycrystalline ceramics such as yttria-stabilized zirconia are covered by the external electrode 23 (a Pt coating) via non-electrolytic plating, the crystal orientation of crystal grains constituting the Pt coating is deduced to develop at random or toward the direction {111}. Since the external electrode 23 (a Pt coating) is heated within the heating temperature range described above, the external electrode 23 (a Pt coating) is subjected to high-temperature heat treatment under a gas atmosphere with higher oxygen concentration than that of the atmospheric gas. As a result, the crystal orientation of the external electrode 23 (a Pt coating) is changed, and the resulting electrode has an increased area of the (001) surface that is advantageous for oxygen dissociation and adsorption.

Since the external electrode 23 (a Pt coating) formed via non-electrolytic platinum plating is constituted by fine Pt particles, the Pt coating is melted under the aging conditions described above, followed by recrystallization. Thus, the crystal orientation of the Pt coating is easily arranged on the (001) surface.

The thus-obtained oxygen sensor can achieve further improved reactivity (sensitivity) to a lean gas existing in the exhaust gas at a very low concentration. Thus, changes of atmospheres in the exhaust gas can be controlled through feedback at an early stage, and stabilized engine system control can be realized. This can reduce fuel consumption and internal combustion engine emissions, compared with conventional oxygen sensors.

In addition, aging of the external electrode 23 (a Pt coating) leads to tempering of the external electrode 23 and the interface between the external electrode 23 and the solid electrolyte 21, and texture is then stabilized. As a result, the external electrode 23 is stabilized in an active state (i.e., a condition that is less likely to change depending on the temperature at which the sensor is used), and changes in sensor properties with the elapse of time are reduced compared with conventional sensors.

EXAMPLES

An oxygen sensor was manufactured in the manner described below. Specifically, a bottomed cylindrical solid electrolyte comprising yttria-stabilized zirconia (YSZ) (5 mol % of yttrium oxide) was molded. Subsequently, an external electrode composed of a Pt coating was provided on the outer surface of the solid electrolyte via non-electrolytic platinum plating. Specifically, an aqueous solution of dinitrodiamineplatinum (2 g/l) was used as a plating solution, and the plating solution was heated to 50 degrees C. Subsequently, an aqueous solution of 80% by mass of hydrazine (4 g/l) as a reducing agent, a stabilizer, and ammonia water (pH 11 to 12) were added to the plating solution, and platinum was deposited on the outer surface of the solid electrolyte without shaking the fixture holding the solid electrolyte. The fixture was not shaken at this time. Thereafter, the resultant was rinsed and dried, and an external electrode having a film thickness of 2 micrometers (Pt coating) was formed. The resulting external electrode was heated with a heater under the ambient atmosphere at 1,000 degrees C. for 1 hour to sinter Pt.

Further, a $MgAl_2O_4$ spinel porous protective layer was provided on the external electrode to a thickness of 200 micrometers via plasma spray coating. In addition, an internal electrode was provided on the inner surface of the solid electrolyte (element) in the same manner as the external electrode (non-electrolytic platinum plating).

The oxygen sensor element provided with the external electrode and the internal electrode was heated in a gas mixture containing nitrogen gas and 50% oxygen by volume (a gas with higher oxygen concentration than that of the atmospheric gas) at 1,100 degrees C. for 1 hour with a heater (i.e., the oxygen sensor element was subjected to the aging treatment). The thus-obtained oxygen sensor element was introduced into the housing to obtain the oxygen sensor.

Comparative Example

An oxygen sensor was manufactured in the same manner as in the example, except that a fixture holding a solid electrolyte was shaken once or twice per second when the external electrode was provided, and the oxygen sensor element provided with the external electrode and the internal electrode was not subjected to the aging treatment.

Reference Example 1

An oxygen sensor was manufactured in the same manner as in the example, except that the oxygen sensor element provided with the external electrode and the internal electrode was not subjected to the aging treatment. In Reference Example 1, the fixture holding a solid electrolyte was not shaken when the external electrode was provided.

Reference Example 2

An oxygen sensor was manufactured in the same manner as in the example, except that a fixture holding a solid electrolyte was shaken once or twice per second when the external electrode was provided. In Reference Example 2, the oxygen sensor element provided with the external electrode and the internal electrode was subjected to the aging treatment.

<Cross Sectional Observation of Pt Coating>

Figure 2:
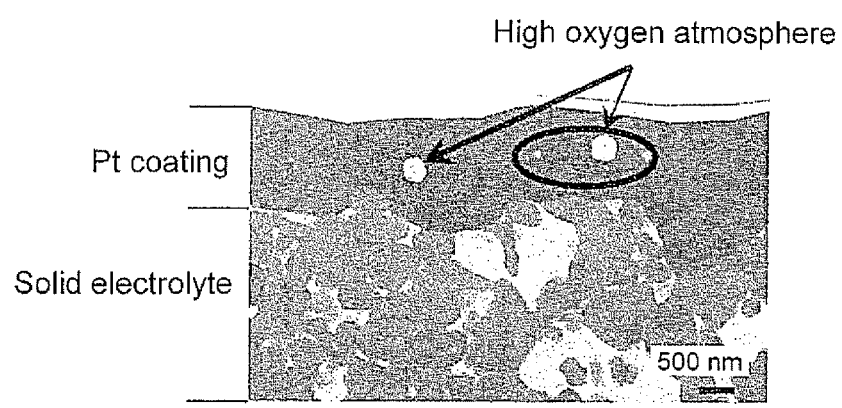
FIG. 2 shows cross-sectional photographs of an example and a comparative example attained with the use of a transmission electron microscope (TEM).
Figure 2:
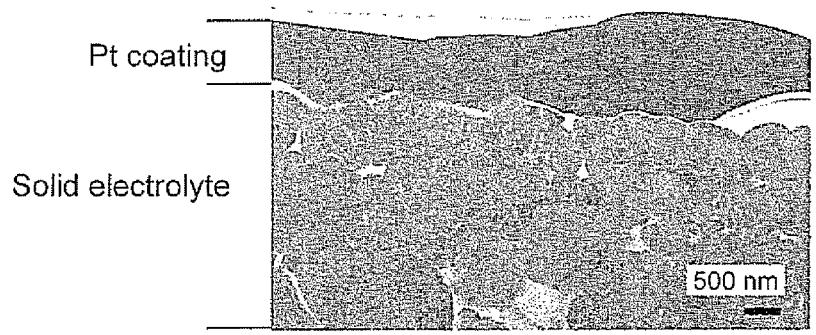

The external electrodes (Pt coatings) according to the example and the comparative example were subjected to cross sectional observation via transmission electron microscope (TEM). FIG. 2 shows photographs showing the cross sections. FIG. 2(a) is a cross sectional photograph of the example and FIG. 2(b) is a cross sectional photograph of the comparative example.

<Determination of Orientation of Pt Coating>

Figure 3:
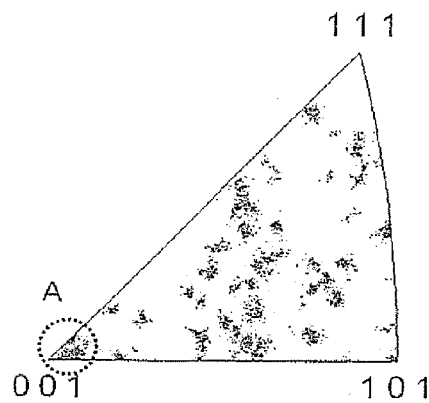
FIG. 3 shows the results of EBSD analysis of electrodes (Pt coatings) provided on the oxygen sensor elements according to Reference Example 2 and a comparative example.
Figure 3:
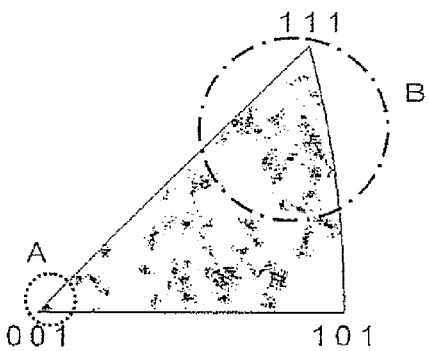

The Pt coating as the external electrode according to Reference Example 2 and that as the external electrode according to the comparative example were each irradiated with electron beams to analyze electron backscatter diffraction patterns (the EBSD method), and the electron backscattered diffraction patterns resulting therefrom were acquired to determine the crystal orientation of the region irradiated with electron beams. FIG. 3 shows the results of EBSD analysis of the electrodes (Pt coatings) provided on the oxygen sensor elements according to Reference Example 2 and the comparative example. FIG. 3(a) is an inverse pole figure attained by EBSD analysis of the electrode (Pt coating) provided on the oxygen sensor element according to Reference Example 2 and FIG. 3(b) is the same according to the comparative example.

<Property Evaluation 1>

Figure 4:
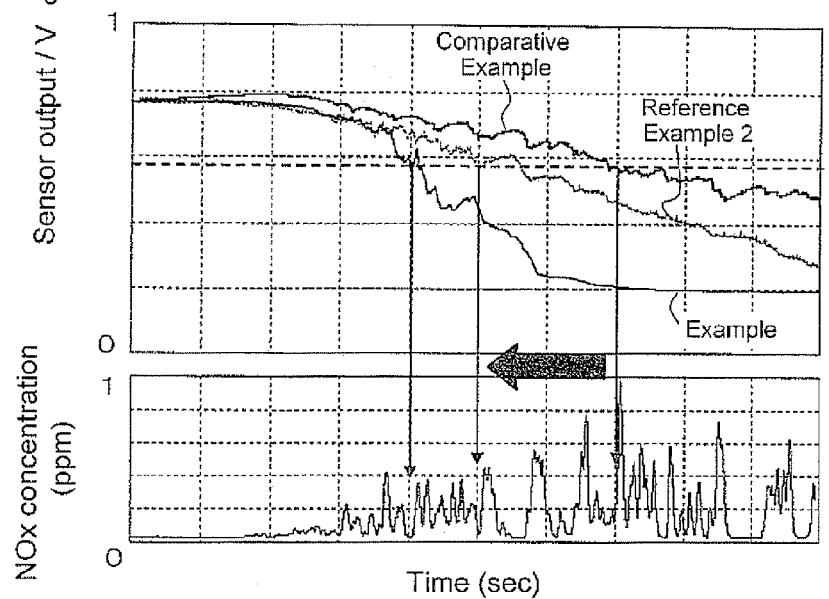
FIG. 4 shows the correlation between sensor output and the amount of gas exhausted when the oxygen sensor according to an example, Reference Example 2, or a comparative example is mounted on actual equipment.

The oxygen sensors according to the example, Reference Example 2, and the comparative example were each mounted on the internal combustion engine (actual equipment), ventilation of the actual equipment was gradually controlled (swept) so as to convert the rich gas atmosphere into a lean gas atmosphere at a level close to the stoichiometric value of A/F=14.6, and the NOx concentration and the output of the oxygen sensors were measured. The results are shown in FIG. 4.

<Property Evaluation 2>

The oxygen sensors according to the example, the comparative example, Reference Example 1, and Reference Example 2 were each mounted on the internal combustion engine (actual equipment), the actual equipment was gradually controlled (swept) so as to convert the rich gas atmosphere into a lean gas atmosphere at a level close to the stoichiometric value of A/F=14.6, and the duration during which rich gas concentration was maintained at a low level while the rich gas atmosphere was converted into a lean gas atmosphere was measured (i.e., the low-concentration rich gas response time).

In contrast, the actual equipment was gradually controlled (swept) so as to convert the lean gas atmosphere into a rich gas atmosphere at a level close to the stoichiometric value of A/F=14.6, and the duration during which rich gas concentration was maintained at a low level while the lean gas atmosphere was converted into a rich gas atmosphere was measured (low-concentration rich gas response time).

Figure 5:
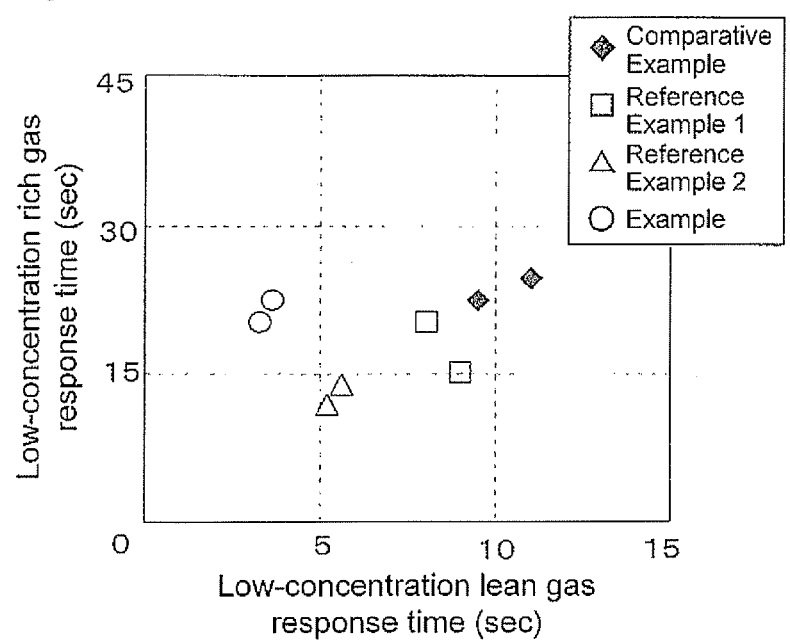
FIG. 5 shows the correlation between low-concentration rich gas and the lean gas response time of the oxygen sensor according to an example, a comparative example, Reference Example 1, or Reference Example 2.

The results are shown in FIG. 5. FIG. 5 shows the correlation between a low-concentration rich gas response time and a low-Concentration lean gas response time of the oxygen sensors according to the example, the comparative example, Reference Example 1, and Reference Example 2.

Results 1 and Discussion 1

As shown in FIG. 2(a), the Pt coating of the example (i.e., the external electrode of the example) was provided with a plurality of closed pores. As shown in FIG. 2(b), the Pt coating of the comparative example (i.e., the external electrode of the comparative example) was not provided with closed pores.

In the case of the example, platinum is deposited on the outer surface without shaking the solid electrolyte during the process of coating. Accordingly, the Pt coating is considered to be provided with a plurality of closed pores. In the case of the example, further, the Pt coating provided on the surface exposed to the gas to be tested is heated under a gas atmosphere with higher oxygen concentration than that of the atmospheric gas in the step of heating. Thus, oxygen gas penetrates and spreads toward the inside of the closed pores from the Pt coating surface. Thereafter, the closed pores are filled with a gas with higher oxygen concentration than that of the atmospheric gas, and, further, oxygen atoms are considered to adsorb to platinum atoms in the vicinity of the closed pores.

Also, it is considered that closed pores are formed on the platinum coating (the external electrode) of Reference Example 1. Since heat treatment is not carried out at a high oxygen concentration in Reference Example 1, the closed pores are not considered to be filled with a gas with a higher oxygen concentration than that of the atmospheric gas. Further, it is considered that closed pores are not formed on the platinum coating (the external electrode) of Reference Example 2.

Results 2 and Discussion 2

As shown in "A" in FIG. 3(a) and in FIG. 3(b), the Pt coating of the oxygen sensor of Reference Example 2 (FIG. 3(a)) exhibited an increased area of a (001) surface of the Pt coating, compared with that of the comparative example (FIG. 3(b)). The Pt coating of the oxygen sensor of the comparative example exhibited an increased (111) area compared with the Pt coating of Reference Example 2, as shown in "B" in FIG. 3(b).

Metal having a crystal structure f.c.c., such as Pt, has low surface energy at the (111) surface and it is deduced to develop toward the direction {111}. While Pt particles grew toward the direction {111} or at random as in the case of the electrode of the oxygen sensor according to the comparative example, the crystal orientation of Pt particles exposed to the oxygen gas changed so as to increase the area of the (001) surface, which is advantageous for oxygen dissociation and adsorption from an energetic point of view, as in the case of Reference Example 2. Thus, it is deduced that the electrode structure as shown in the inverse pole figure of FIG. 3(a) is attained.

The oxygen sensor according to the example that had been subjected to the aging treatment under similar heating conditions is also considered to have an increased area of the (001) surface of the Pt coating. Since ozone gas is degraded into oxygen gas at the heating temperature employed for the aging treatment of the Pt coating, it is deduced that results similar to those obtained in the example are attained via, for example, introduction of ozone gas before the aging treatment to bring the oxygen gas concentration to a level higher than the oxygen concentration of the atmospheric gas at the time of ozone gas degradation.

Results 3 and Discussion 3

As shown in FIG. 4, the responsiveness of the oxygen sensor was elevated in accordance with changes in NOx concentration in the order of the oxygen sensor of the example, that of Reference Example 2, and that of the comparative example. The results indicate that the oxygen sensor of the example and that of Reference Example 2 exhibit higher responsiveness to changes in NOx concentration than that of the comparative example, since the crystal orientation of the Pt coating (the external electrode) is arranged in the direction of (001) via the step of heating (aging treatment). In addition, the oxygen sensor of the example is considered to exhibit elevated responsiveness to changes in NOx concentration than that of Reference Example 2 due to the provision of oxygen-containing closed pores inside the Pt coating (the external electrode) of the example.

Results 4 and Discussion 4

As shown in FIG. 5, the rich gas response time of the oxygen sensor of the example was equivalent to or slower than that of the oxygen sensor of the comparative example, Reference Example 1, or Reference Example 2, and the lean gas response time thereof was improved. The lean gas response time of the oxygen sensor of Reference Example 1 was improved over that of the comparative example.

As described in the Discussion 3 above, the responsiveness of the oxygen sensor of the example to conversion of the rich gas atmosphere into a lean gas atmosphere was improved compared with that of Reference Example 2 due to the provision of oxygen-containing closed pores inside the Pt coating (the external electrode) of the example. Further, moderate responsiveness of the oxygen sensor to conversion of the lean gas atmosphere into a rich gas atmosphere can be achieved, according to FIG. 5.

As is apparent from the results attained in the comparative example and Reference Example 1, the responsiveness of the oxygen sensor to conversion of the rich gas atmosphere into a lean gas atmosphere is elevated due to the provision of oxygen-free closed pores inside the coating. If oxygen-containing closed pores are provided inside the coating, accordingly, the responsiveness of the oxygen sensor to conversion of the rich gas atmosphere into a lean gas atmosphere is elevated compared with the oxygen sensor according to the comparative example without the aging treatment of the Pt coating (the external electrode). Further, it is considered that moderate responsiveness of the oxygen sensor to conversion of the lean gas atmosphere into a rich gas atmosphere can be achieved.

The Pt coating changes so as to increase the area of the (001) surface, which is advantageous for oxygen dissociation and adsorption from an energetic point of view, via the aging treatment as in the case of the example and Reference Example 2. Thus, the responsiveness to conversion of the rich gas atmosphere into a lean gas atmosphere is considered to be improved.

The present invention had been described in detail with reference to the embodiments of the present invention above. It should be noted that concrete constitutions are not limited to the embodiments and the examples, and modifications in design that do not depart from the present invention are within the scope of the present invention.

REFERENCE SIGNS LIST

1: Oxygen sensor
11: Oxygen sensor element
12: Cover for gas to be tested
12a: Introduction port for gas to be tested
21: Solid electrolyte
22: Air chamber
23: External electrode (Pt coating)
23a: Closed pores
24: Internal electrode

The invention claimed is:
1. A method for manufacturing an oxygen sensor equipped with an oxygen sensor element comprising a solid electrolyte and Pt coatings, as a pair of electrodes, on both surfaces thereof,
the method comprising at least steps of:
providing a Pt coating on at least one of the solid electrolyte surfaces exposed to the gas to be tested so as to form closed pores inside the Pt coating; and
heating the Pt coating provided on at least the surface exposed to the gas to be tested in a gas atmosphere with higher oxygen concentration than that of the atmospheric gas, and
wherein the step of coating is carried out via non-electrolytic platinum plating, and the closed pores are provided inside the Pt coating by bubbling non-oxidizing gas through a plating solution when conducting non-electrolytic platinum plating.
2. The method for manufacturing an oxygen sensor according to claim 1, wherein the step of heating is carried out at 1,000 degrees C. to 1,300 degrees C. for at least 1 hour.

* * * * *